United States Patent [19]

Bohen et al.

[11] Patent Number: 5,086,098

[45] Date of Patent: Feb. 4, 1992

[54] POLYHALOAROMATIC ESTER FLAME RETARDANTS FOR POLYOLEFIN RESINS

[75] Inventors: Joseph M. Bohen, King of Prussia, Pa.; Gerald H. Reifenberg, East Windsor, N.J.

[73] Assignee: Atochem North America, Inc., Philadelphia, Pa.

[21] Appl. No.: 622,122

[22] Filed: Dec. 3, 1990

Related U.S. Application Data

[63] Continuation of Ser. No. 322,035, Mar. 10, 1989, abandoned, which is a continuation-in-part of Ser. No. 3,839, Oct. 28, 1989, abandoned, which is a continuation-in-part of Ser. No. 115,211, Oct. 30, 1987, Pat. No. 4,762,861, and Ser. No. 115,688, Oct. 30, 1987, Pat. No. 4,938,894, and Ser. No. 173,344, Mar. 25, 1988, Pat. No. 4,912,158, and Ser. No. 173,691, Mar. 25, 1988, Pat. No. 4,923,917, and Ser. No. 173,343, Mar. 25, 1988, Pat. No. 4,954,542, which is a continuation-in-part of Ser. No. 244,421, Sep. 16, 1988, Pat. No. 5,049,697.

[51] Int. Cl.$^5$ ............................ C08K 5/20; C08K 5/12
[52] U.S. Cl. ...................................... 524/94; 524/281; 524/371; 524/410; 524/411; 524/412; 524/467
[58] Field of Search ................. 524/219, 288, 281, 94, 524/371, 410, 411, 412, 467

[56] References Cited

U.S. PATENT DOCUMENTS 2,496,852  2/1950  Buhrer .
3,772,342  11/1973  Foley .................... 260/475
3,775,165  11/1973  Young et al. .......... 524/288
3,966,676  6/1976  Richter .................. 260/45.75
4,094,850  6/1978  Morgan et al. ........ 524/288
4,098,704  7/1978  Sandler ................... 560/83
4,125,733  11/1978  Sandler ................. 524/288
4,298,517  11/1981  Sandler ................. 524/296
4,361,666  11/1982  Dufour .................. 524/295
4,376,837  3/1983  Jenkins et al. ........ 524/108
4,397,977  8/1983  Sandler ................. 524/288
4,762,861  8/1988  Bohen et al. .......... 524/140
4,912,158  3/1990  Bohen et al. .......... 524/412
4,923,916  5/1990  Bohen et al. .......... 524/217
4,923,917  5/1990  Bohen et al. .......... 524/412
4,927,873  5/1970  Bohen et al. .......... 524/412

*Primary Examiner*—Veronica P. Hoke
*Attorney, Agent, or Firm*—Panitch Schwarze Jacobs & Nadel

[57] ABSTRACT

Flame retardant compositions are provided containing at least one ester of a polyhaloaromatic acid and at least one polyolefin resin. The compositions may also contain one or more brominated and/or chlorinated compounds to provide additional flame retardancy, and other resins or engineering thermoplastics may be blended with the polyolefin. In addition to providing flame retardancy, the polyhaloaromatic acid esters are effective as processing and compatibilizing aids for the resin, and may also function as tackifiers, mold release agents, plastisole, adhesives, plasticizers, polymer additives, and aids in preventing melt fracture.

20 Claims, No Drawings

POLYHALOAROMATIC ESTER FLAME RETARDANTS FOR POLYOLEFIN RESINS

CROSS REFERENCE TO RELATED APPLICATIONS

This application is a continuation of U.S. patent application Ser. No. 07/322,035 now abandoned, which in turn is a continuation-in-part of copending International Application No. PCT/US88/03839, filed in the United States on Oct. 28, 1988 for "Tetrahalophthalate Esters as Flame Retardants for Certain Resins," now abandoned which claimed priority as a continuation-in-part of: U.S. application Ser. No. 115,211 filed Oct. 30, 1987 now U.S. Pat. No. 4,762,861; U.S. application Ser. No. 115,688 filed Oct. 30, 1987 now U.S. Pat. No. 4,938,894; U.S. application Ser. No. 173,344 filed Mar. 25, 1988 now U.S. Pat. No. 4,912,158; U.S. application Ser. No. 173,691 filed Mar. 25, 1988 now U.S. Pat No. 4,923,917; and U.S. application 173,343 filed Mar. 25, 1988 now U.S. Pat. No. 4,954,542. This application is also a continuation-in-part of copending U.S. patent application Ser. No. 244,421 filed Sept. 16, 1988, now U.S. Pat. No. 5,049,697 for "High Yield Method for Preparation of Dialkyl Esters of Polyhaloaromatic Acids". This application is also related to U.S. application Ser. No. 258,267, filed Oct. 14, 1988, now abandoned, and refiled as Ser. No. 508,744, on Apr. 12, 1990, by Joseph M. Bohen for "Fire Resistant Hydraulic Fluids." The disclosures of the above applications are incorporated herein by reference. The claimed invention of the present application and the subject matter of the above-identified applications were commonly owned or subject to an obligation of assignment to the same entity at the time the present invention was made.

FIELD OF THE INVENTION

The present invention relates to flame retardant compositions containing at least one halogen-substituted compound and a polyolefin resin. More particularly, the invention is directed to methods and compositions for improving the flame retardancy and processability of polyolefin resins using halogen-substituted compounds.

BACKGROUND OF THE INVENTION

The use of brominated and/or chlorinated compounds by themselves or in combination with other materials such as organic phosphates, boron compounds, etc., as flame retardants for resin compositions is well known in the art. For example, U.S. Pat. No. 3,775,165 of Young et al. describes halogenated aromatic dicarboxylic acid diesters useful for improving the flame retarding and dyeing properties of polyester fibers and polypropylene polymers and fibers.

Further, tetrahalophthalate esters have been used as flame-proofing materials. For example, U.S. Pat. No. 4,098,704 of Sandler describes the use of these materials as textile finishing agents. U.S. Pat. Nos. 4,298,517 and 4,397,977 of Sandler disclose these compounds as flame retardants for halogenated resins. U.S. Pat. No. 4,762,861 of Bohen et al. discloses tetrahalophthalate esters as flame retardant processing aids for polystyrene resins.

Polyhalophenyl esters have been used as flame-proofing materials either as additives to plastics or incorporated as part of the polymer backbone. Examples of the latter are polyhalophenyl esters of polymerizable acids such as 2,4,6-tribromophenyl methacrylate, pentabromophenyl methacrylate, 2,4,6-tribromophenyl acrylate, pentachlorophenyl methacrylate, pentabromophenyl acrylate, trichlorophenyl acrylate, tetrabromoxylene di(methacrylate), etc., which are exemplified by U.S. Pat. Nos. 3,207,731; 3,210,326; 3,845,102; 3,932,321; 4,032,509; 4,048,263; 4,105,628; 4,108,943; 4,110,296; 4,205,153; and 4,415,704, the disclosures of which are incorporated herein by reference.

Examples of polyhalophenyl esters that have been used as additives to plastics are pentabromophenyl 2,4,4,4-tetrachlorobutyrate, bis(2,4,6-tribromophenyl) tetrachloroterephthalate, pentabromophenyl o-(2,4,6-tribromophenoxymethyl) benzoate, pentabromophenyl o-(pentachlorophenylthiomethyl) benzoate, bis(2,4,6-tribromophenyl) isophthalate, bis(pentabromophenyl) terephthalate, 2,4,6-tribromophenyl 3,5-dibromobenzoate, 2,4,6-tribromophenyl tribromopivalate, pentachlorophenyl tribromopivalate, bis(2,4,6-trichlorophenyl) phthalate, bis(2,4,6-tribromophenyl) phthalate, pentachlorophenyl acetate, bis(2,4,6-tribromophenyl) sebacate, and pentabromophenyl acetate, etc. which are exemplified by U.S. Pat. Nos. 3,275,578; 3,660,351; and 3,804,885, as well as Eur. Pat. Appl. EP73539; Japan Kokai JP 55/56140; 53/120755; 51/86554; 51/23545; 50/90639; 50/95353; 50/87146; 48/101443 and 47/46478; and Ger. Offen. DE 2,554,513 and DE 2,161,526, the disclosures of which are incorporated herein by reference.

Halogen substituted phthalimides have also been used as flame-proofing materials. For example, U.S. Pat. No. 3,873,567 describes the use of these materials as flame retardants in polymers, etc., especially polypropylene. U.S. Pat. No. 4,374,220 describes the use of halosubstituted mono- and bis-phthalimides for polyethylene, polypropylene, ethylene-propylene copolymers, etc. British Patent 2,114,127 describes carbonate-substituted polyhalophthalimides as flame retardants for polyethylene, among others.

BRIEF SUMMARY OF THE INVENTION

According to the present invention, flame retardant compositions are provided in which a polyolefin resin is blended with a flame retarding amount of a polyhaloaromatic acid ester of the following general formula:

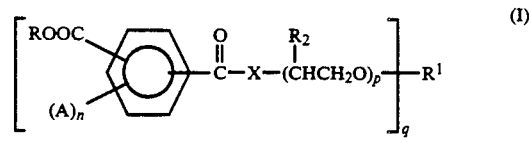

(I)

wherein
(a) the ring can have all possible isomeric arrangements
(b) R is selected from the group consisting of alkyl or substituted alkyl of 1 to 30 carbons, and

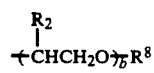

wherein $R^8$ is an alkyl or substituted alkyl of 1 to 18 carbons, and b is 1 to 50;
(c) $R^1$ is selected from the group consisting of alkyl or substituted alkyl of 1 to 30 carbons, alkenyl or substituted alkenyl of 2 to 22 carbons,

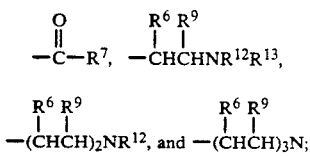

with the proviso that the valence of $R^1$ is equal to q;

(d) $R^2$ is independently selected from the group consisting of H and $CH_3$;

(e) $R^6$, $R^9$, $R^{12}$ and $R^{13}$ are independently hydrogen or alkyl of 1 to 22 carbons, $R^7$ is an alkyl of 1 to 18 carbons;

(f) p is an integer of 0 to 50;

(g) q is an integer of 1 to 6;

(h) A is halogen;

(i) X is O or NH; and (j) n=1 to 4.

The polyhaloaromatic acid esters of the above formula are not only effective to increase the flame retardancy of the polyolefin resins but are also completely compatible with the resins and may serve as tackifiers, mold release agents, plastisols, adhesives, plasticizers, polymer additives, and aids in preventing melt fracture. Moreover, it has been unexpectedly found that the esters improve the impact strength of the polyolefins.

Further, the polyolefin compositions of the present invention may be blended with other resins and engineering thermoplastics, and additional flame retarding additives besides the polyhaloaromatic acid esters may be used. Preferably, the esters contain at least 25 weight percent bound halogen, and more preferably at least 35 weight percent bound bromine.

DETAILED DESCRIPTION OF PREFERRED EMBODIMENTS

The resins which can be made flame retardant by incorporating polyhaloaromatic acid esters according to this invention are any readily flammable polyolefin resins or resin blends including polyolefins. Exemplary of the polyolefins and blends which can be flameproofed include saturated, unsaturated, linear, atactic, crystalline or non-linear amorphous polymers, copolymers, terpolymers, etc. for example polyethylene, polypropylene, poly(4-methylpentene-1), polybutene-1, polyisobutylene, ethylene-propylene-copolymer, cis-1-4-polyisoprene, ethylene-propylene-dicyclopentadiene terpolymer, etc. and blends of these polymers with each other or with other polymers.

Particularly preferred polyolefin resins that may be used in this invention are (a) polyethylene which includes all grades, such as low density, linear low density, and high-density grades, (b) polypropylene, (c) ethylene propylene copolymers, (d) ethylene-vinyl acetate copolymers, (e) polyvinyl acetate, (f) polyvinyl alcohol, (g) poly-4-methylpentene-1, (h) polyisobutylene, and substituted polyolefins, such as (i) polyacrylate esters, and (j) polymethacrylate esters. Combinations of any of the above polyolefins (a to j) by themselves or blends with polystyrenes, styrene-butadiene copolymers, chlorinated polyethylene, polyvinyl chloride, or engineering thermoplastics such as acrylonitrile-styrene-butadiene (ABS), polybutylene terephthalate (PBT), polyphenylene oxides (PPO), polyphenylene oxides—high impact polystyrene (PPO-HIPS), etc., are conceived as falling within the scope of this invention.

The uses and applications of the polyolefin resins of this invention are well known to those skilled in the art. They are discussed, for example, in G. Hawley, Condensed Chemical Encyclopedia, 10th Edition (1981), p. 17 (polyacrylate and polymethacrylate esters), p. 435 (ethylene-propylene and ethylene-vinyl acetate copolymers), p. 829 (polyisobutylene), pp. 830-831 (polyethylene), p. 835 (poly-4-methylpentene-1), p. 837 (polypropylene), p. 840 (polyvinyl alcohol and polyvinyl acetate). The preparation and description of the polyolefin resins that are suitable for use in this invention are also well known in the art. They are discussed, for example, in the *Encyclopedia of Polymer Science and Engineering*, 2nd Edition, Vol. 1 (1985), pp. 236-305 (polyacrylate and polymethacrylate esters); Vol. 6 (1986), pp. 383-521 (polyethylenes), pp. 408, 421-22 (ethylene-polyvinyl acetate), pp. 522-564 (ethylene-propylene copolymers); Vol. 8, pp. 423-448 (polyisobutylene); Vol. 9, pp. 707-18 (poly-4-methylpentene-1); *Encyclopedia of Chemical Technology*, 3rd Edition, Vol. 23 (1983), pp. 817-865 (polyvinyl alcohol and polyvinyl acetate).

The polyhaloaromatic acid esters useful in the present invention are known in the art from prior patents and patent applications of Pennwalt Corporation, the assignee of the present invention. In particular, such esters and their methods of manufacture are described in U.S. Pat. No. 4,764,550 of Lovenguth, particularly in specific examples 47, 48, and 80-83, and U.S. Ser. No. 258,267 now abandoned particularly in specific examples 22, 24-27 and 30-60, the disclosures of which are incorporated herein by reference. Improved high-yield methods of producing these esters are disclosed in U.S. Ser. No. 244,421 now U.S. Pat. No. 5,049,697.

Preferred esters of polyhaloaromatic acid esters useful in the present invention are those of formula I above wherein R is an alkyl or substituted alkyl of 1 to 10 carbons, A is bromine, n is 4, X is oxygen, p is 0 to 20, and q is 1 to 6. More preferably, R and R are independently selected from $-CH_3$, $-C_2H_5$, $-C_3H_7$, $-C_4H_9$, $-C_6H_{13}$, $-CH_8H_{17}$,

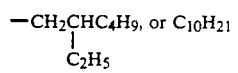

Examples of representative polyhaloaromatic acid esters of the present invention include the following, wherein A is Br or Cl and "av" indicates average or approximate numbers of units since the products are often mixtures of compounds:

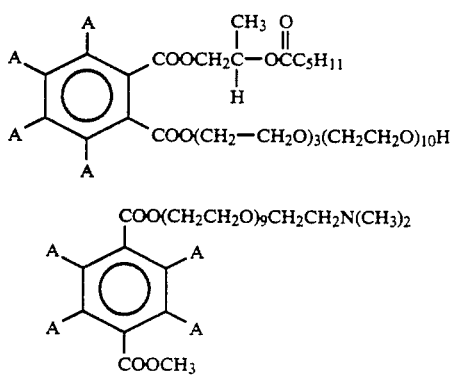

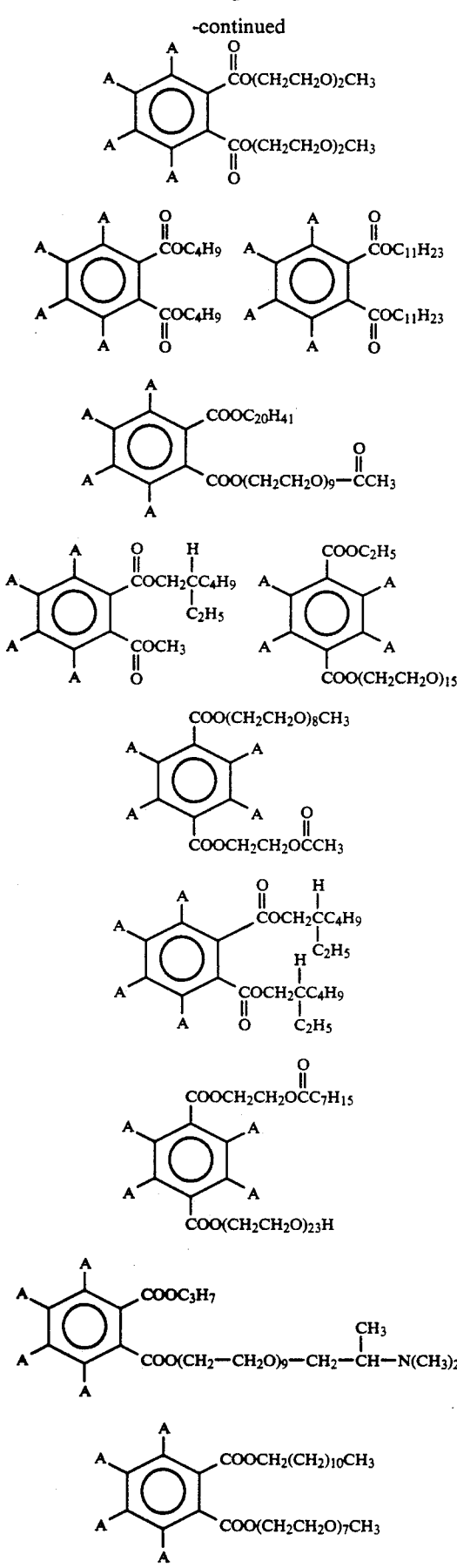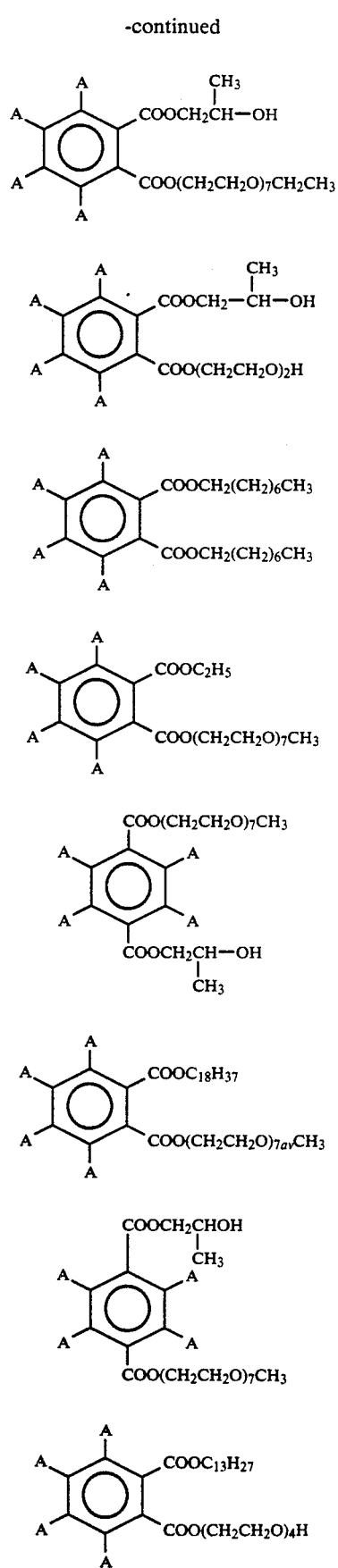

-continued
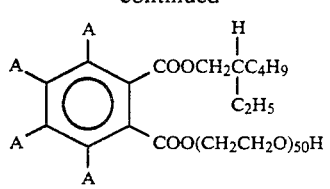
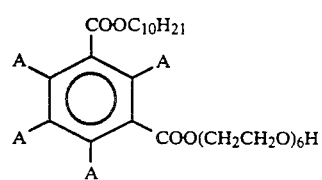
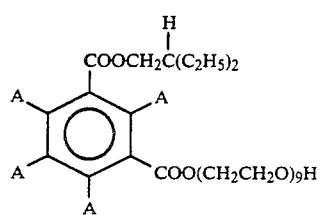
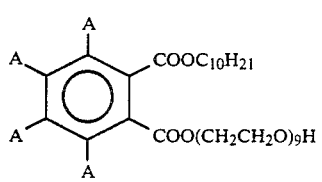
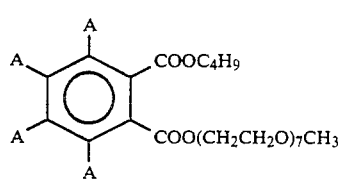
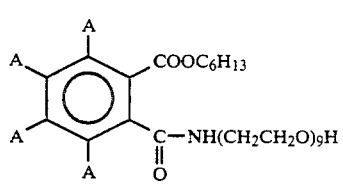
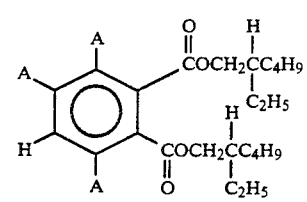
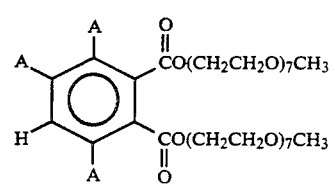
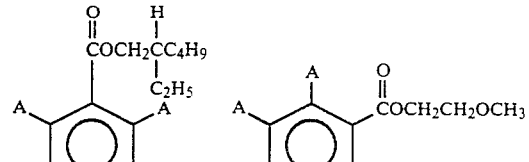
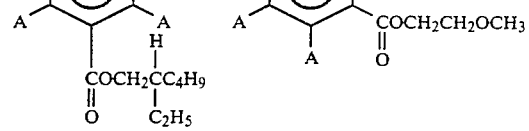
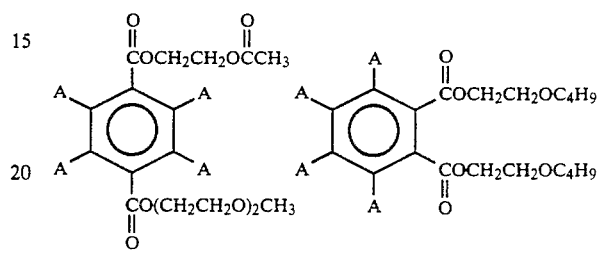
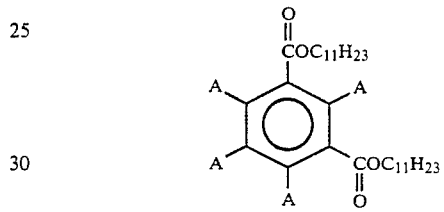
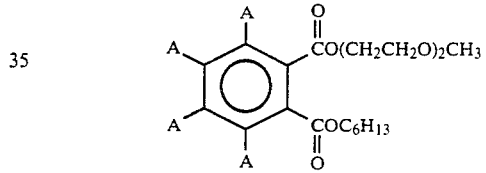
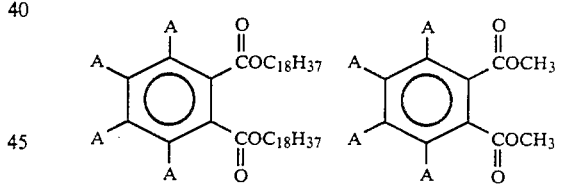
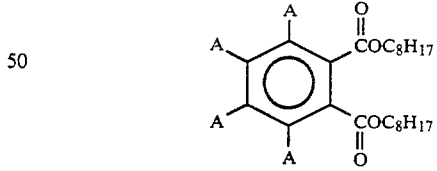
Preferred Examples of the esters are as follows:
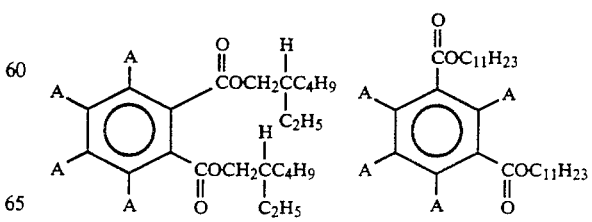

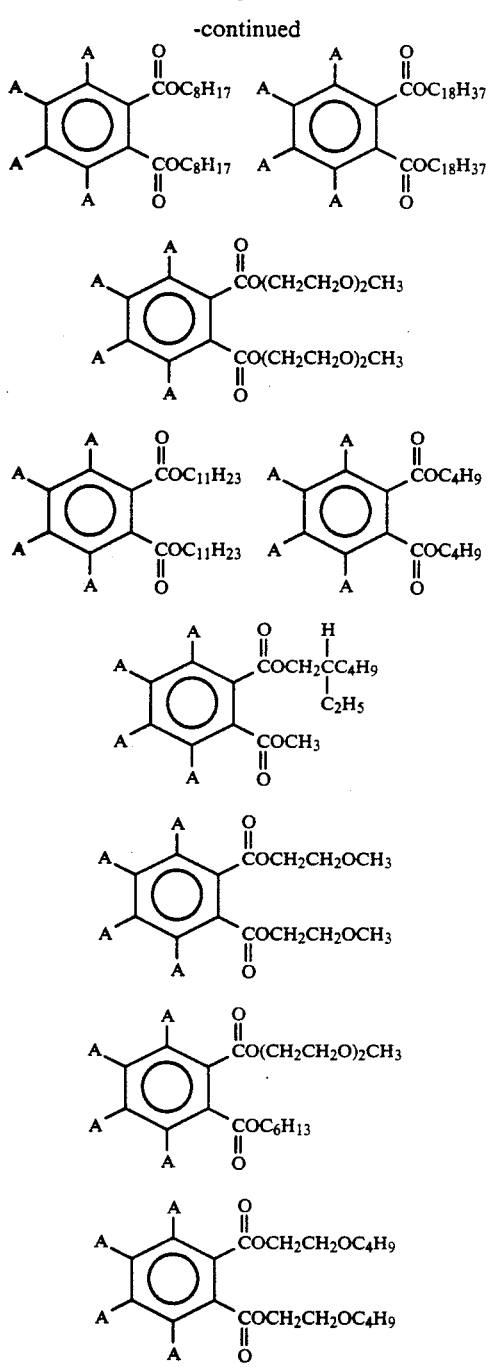
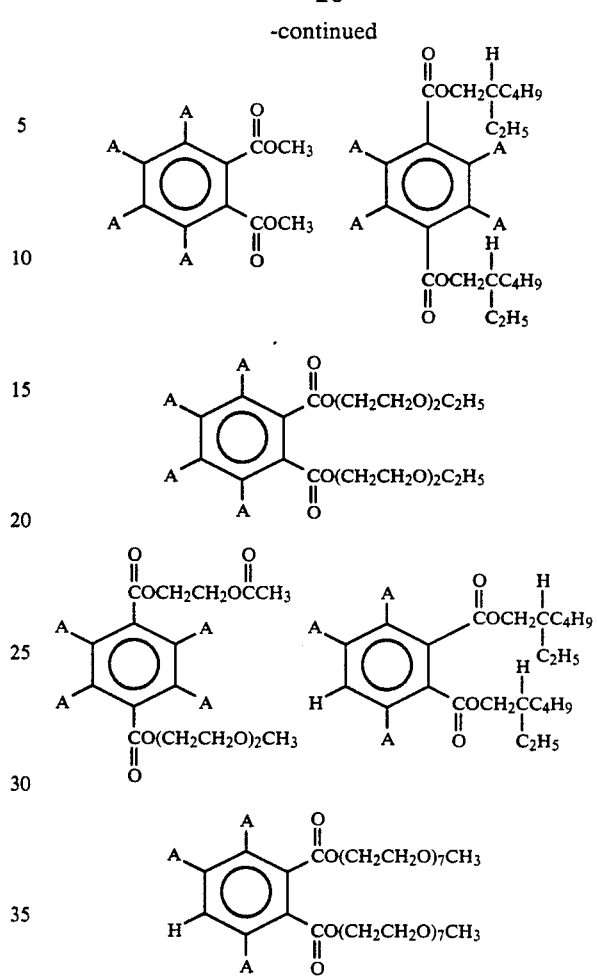

The halogen substituents on the esters of polyhaloaromatic acids useful in the present invention are preferably selected from chlorine and bromine. Moreover, it is desirable that the halogen substituents comprise a large percentage of the esters of this invention, preferably at least about 25 weight percent bound halogen in the esters. In the case of the preferred bromine-substituted esters described below, the bound bromine should preferably comprise at least 35 weight percent and may comprise in excess of the 40 or 45 weight percent of the ester. The high weight percent of halogen is important since the halogen is believed to be largely responsible for the flame retarding properties.

Another aspect of this invention is that the compositions may optionally contain other bromine and/or chlorine flame retardant compounds such as those that are well known in the art. Examples of such compounds include the following:

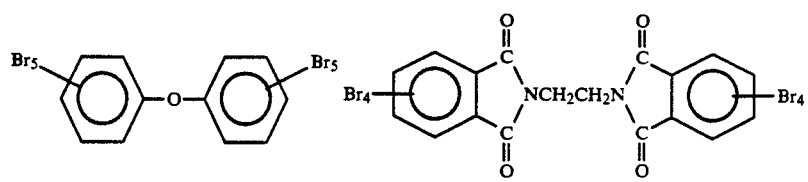

-continued
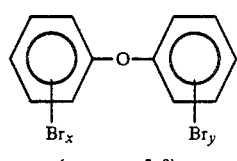
(x + y = 5-8)
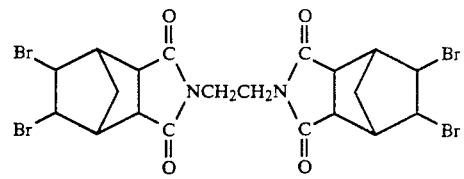
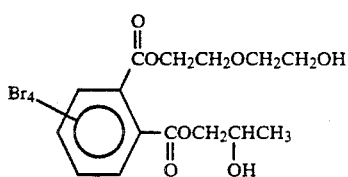
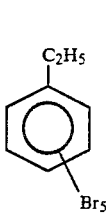
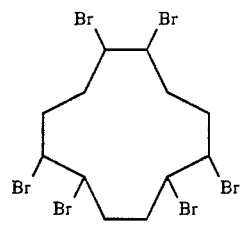
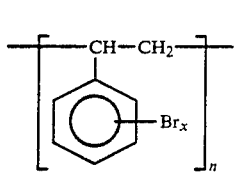
x = 1,2,3
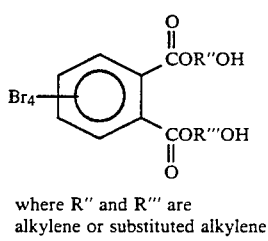
where R″ and R‴ are
alkylene or substituted alkylene
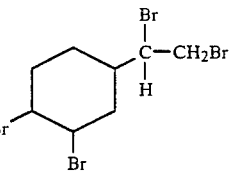
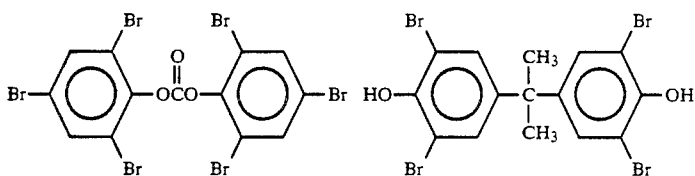
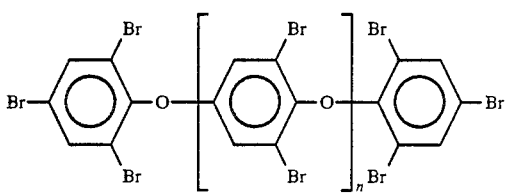
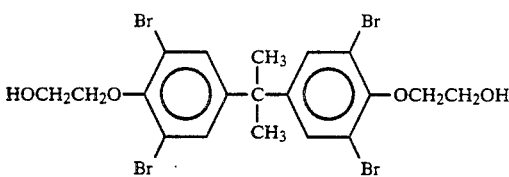
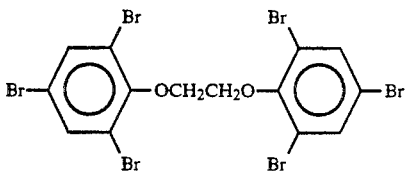
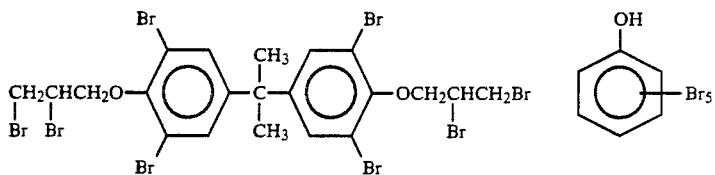
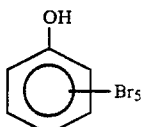

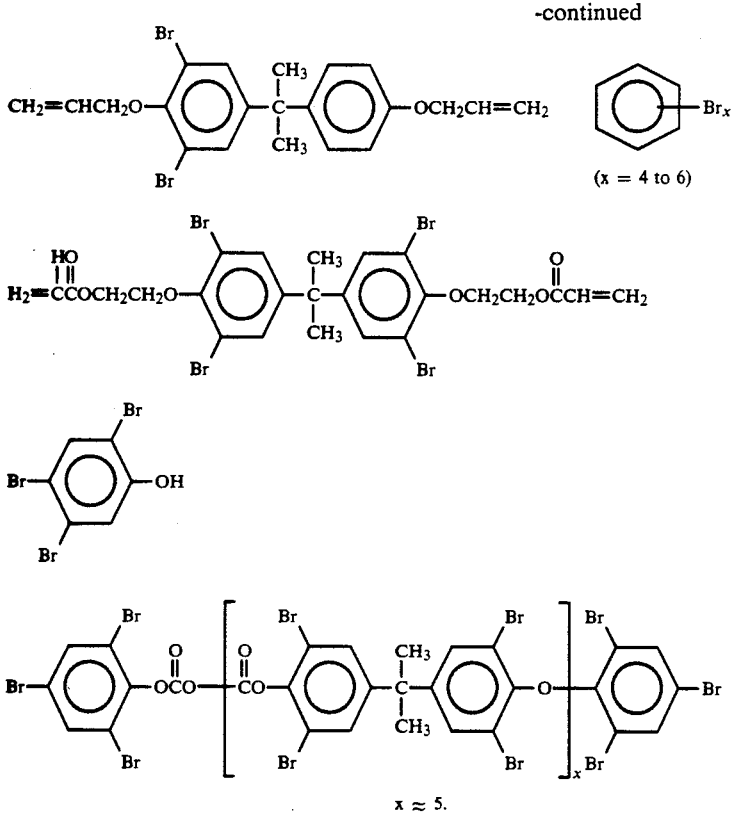

(x = 4 to 6)

x ≈ 5.

In practicing this invention, the polyhaloaromatic acid ester is added to the polyolefin resin or blend in any convenient manner, such as blending, extruding, kneading, etc. in order to produce a uniform composition. Flame retardant synergists such as antimony oxide ($Sb_2O_3$) may also be added if desired. In addition, other additives such as thermal stabilizers, ultraviolet stabilizers, reinforcing agents, organic polymers, mold release agents, blowing agents, colorants, and the like may also be optionally included.

However, as noted above, the polyhaloaromatic acid ester flame retardants themselves function as processing aids and compatibilizers for the polyolefin resins and blends, and may also function as tackifiers, mold release agents, plastisols, alhesives, plasticizers, polymer additives, and aids in preventing melt fracture.

The polyhaloaromatic acid ester is added to the polyolefin resin or blend in an amount effective to increase the flame retardancy of the composition. The exact amount necessary will vary with the particular resin and compound of the invention used. Generally, ratios of ester to resin in the range of about 1:100 to about 1:2 and preferably about 1:4 to 1:20, will be effective depending upon the particular application.

In addition to providing increased flame retardancy to thermoplastic resins, the polyhaloaromatic acid esters of the present invention are advantageous as processing aids to improve the flowability or moldability of the resin during melt processing, such as extrusion or injection molding.

EXPERIMENTAL EXAMPLES A-E

In the following examples, the flame retardancy of the compositions of this invention are demonstrated. The compositions were prepared by mixing together the flame retardants, antimony oxide, and polypropylene resin on a roller until the compounds were blended thoroughly. The compounds were pelletized at 235°-250° C. and then injection molded into test specimens at 177°-193° C. The UL-94 (Underwriters Laboratory Bulletin No. 94) vertical burn test was run and compared to a control consisting of only polypropylene resin and antimony oxide. The following tests were performed on the various materials according to the appropriate ASTM method, and the results are reported in Table I below, where each component is listed in parts by weight.

1. Limited Oxygen Index (LOI)—ASTM D-2863
2. Impact Strength—Notched Izod—ASTM D-256
3. Impact Strength—Gardner—ASTM D-3029
PP=Polypropylene (Himont's PROFAX 6501)
AO=Antimony Oxide
DBDPO=Decabromodiphenyl Oxide (83% Br)
DOTBP=Di-2-ethylhexyltetrabromophthalate (45% Br), also referred to as dioctyl tetrabromophthalate.

Table I clearly demonstrates the significant improvement in the flame retardancy of the compositions of this invention relative to the control (Example A), as indicated by the 50% higher LOI values and the fact that the control failed the UL-94 tests while the compositions of this invention passed them.

Examples B-E were all run at equal bromine levels. Decreasing the ratio of the conventional flame retardant (DBDPO) to that of DOTBP greatly increases the impact strength (Notched Izod and Gardner) of polypropylene.

TABLE I

| | Sample No. | | | | |
|---|---|---|---|---|---|
| | A | B | C | D | E |
| PP | 85 | 85 | 85 | 85 | 85 |
| DBDPO | | 43 | 39 | 35 | 30 |

TABLE I-continued

| | Sample No. | | | | |
|---|---|---|---|---|---|
| | A | B | C | D | E |
| DOTBP | | | 11.9 | 23.5 | 40 |
| AO | 15 | 15 | 15 | 15 | 15 |
| UL-94 at 0.125" | Fail | V-O | V-O | V-O | V-O |
| UL-94 at 0.062" | Fail | V-O | V-O | V-O | V-O |
| LOI | 17.5 | 26.0 | 26.0 | 26.5 | 26.5 |
| Notched Izod Impact (ft-lbs/in Notch) | .33 | .29 | .37 | .44 | .62 |
| Gardner Impact (in-lbs) | 12 | 10.7 | 12 | 37.6 | 127.3 |

EXPERIMENTAL EXAMPLES F-J

In the following examples, the flame retardancy of the compositions of this invention are further demonstrated. The compositions were prepared by mixing together the flame retardants, antimony oxide, talc, (Cyprus, MISTRON 400) and polypropylene resin on a roller until the compounds were blended thoroughly. The compounds were pelletized at 200°-260° C. and then injection molded into test specimens at 171°-193° C. The UL-94 vertical burn test was run and compared to a control consisting of only polypropylene resin, talc and antimony oxide. The same tests were performed on these materials as on the compositions of Examples A-E, and the results are shown in Table II below.

TABLE II

| | Sample No. | | | | |
|---|---|---|---|---|---|
| | F | G | H | I | J |
| PP | 76 | 76 | 76 | 76 | 76 |
| DBDPO | | 25 | 20 | 15 | 10 |
| DOTBP | | | 11.3 | 22.6 | 33.9 |
| AO | 6 | 6 | 6 | 6 | 6 |
| Talc | 18 | 18 | 18 | 18 | 18 |
| UL-94 at 0.125" | Fail | V-O | V-O | V-O | V-O |
| UL-94 at 0.062" | Fail | Fail | V-2 | V-2 | V-2 |
| LOI | 19.5 | 24.0 | 24.0 | 24.0 | 23.5 |
| Notched Izod Impact (ft-lbs/in Notch) | 0.3 | 0.26 | 0.60 | 0.68 | 0.68 |
| Gardner Impact (in-lbs) | 9.3 | <8 | <8 | ~12 | 29.8 |

Table II clearly demonstrates the significant improvement in flame retardancy of the compositions of this invention (Examples G-I) relative to the control (Example F) and to the conventional flame retardant, DBDPO. The control sample failed the UL-94 test while the compositions of this invention passed them. Also DBDPO failed the UL-94 test at 0.062" which is more stringent than at 0.125". The compositions of this invention show 20-23% higher LOI values than the control.

Examples G-I were all run at equal bromine levels. Replacing a portion of the DBDPO with the flame retardants of this invention (DOTBP) greatly increases the Notched Izod Impact of polypropylene. A similar trend is shown with the Gardner impact data at the two highest loadings of DOTBP (Examples I and J).

The present invention may be embodied in other specific forms without departing from the spirit or essential attributes thereof and, accordingly, reference should be made to the appended claims, rather than to the foregoing specification as indicating the scope of the invention.

We claim:

1. A flame retardant composition comprising a uniform blend of a polyolefin resin and an amount of an ester of a polyhaloaromatic acid of the following general formula to increase the flame retardancy in said resin:

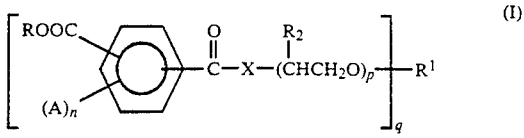

wherein
(a) the ring can have all possible isomeric arrangements;
(b) R is selected from the group consisting of alkyl or substituted alkyl or 1 to 30 carbons with the proviso that said alkyl is not substituted with a hydroxy group or a halogen, and

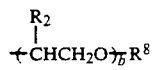

wherein $R^8$ is an alkyl or substituted alkyl of 1 to 18 carbons, and b is 1 to 50 with the proviso that said alkyl is not substituted with a hydroxy group or a halogen;
(c) $R^1$ is selected from the group consisting of alkyl or substituted alkyl or 1 to 30 carbons, alkenyl or substituted alkenyl of 2 to 22 carbons with the proviso that said alkyl and alkenyl are not substituted with a hydroxy group or a halogen,

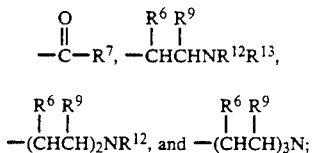

with the proviso that the valence of $R^1$ is equal to q;
(d) $R^2$ is independently selected from the group consisting of H and $CH_3$;
(e) $R^6$, $R^9$, $R^{12}$ and $R^{13}$ are independently hydrogen or alkyl of 1 or 22 carbons, $R^7$ is an alkyl of 1 to 18 carbons;
(f) p is an integer of 0 to 50;
(g) q is an integer of 1 to 6;
(h) A is halogen;
(i) X is O or NH; and
(j) n=1 to 4.

2. A composition according to claim 1 wherein A is chlorine or bromine and said ester of a polyhaloaromatic acid contains at lest 25% by weight of bound halogen.

3. A composition according to claim 2, wherein A is bromine and the ester of a polyhaloaromatic acid contains at least about 35 weight percent bound bromine.

4. A composition according to claim 1 wherein said polyolefin resin is selected from the group consisting of polyethylene, polypropylene, ethylene-propylene copolymers, polyvinyl acetate, ethylene-vinyl acetate copolymers, polyvinyl alcohol, poly-4-methylpentene-1, polyisobutylene, acrylate ester polymers, methacrylate ester polymers, and blends of the above.

5. A composition according to claim 1 wherein the weight ratio of ester of polyhaloaromatic acid to polyolefin resin is within the range of about 1:100 to about 1:2.

6. A composition according to claim 1 wherein said polyolefin resin is blended with a resin selected from the group consisting of polystyrene, styrene-butadiene copolymers, chlorinated polyethylenes, polyvinyl chloride, acrylonitrile-styrene-butadiene terpolymers, polybutylene terephthalate, polyphenylene oxides, polyphenylene oxide—high impact polystyrene blends, and mixtures thereof.

7. The composition of claim 1 wherein R is an alkyl or substituted alkyl of 1 to 10 carbons, A is Br, n is 4, X is oxygen, p is 0 to 20, and q is 1 to 6.

8. The composition of claim 7, wherein R and R$^1$ are independently selected from —CH$_3$, —C$_2$H$_5$, —C$_3$H$_7$, —C$_4$H$_9$, —C$_6$H$_{13}$, —C$_8$H$_{17}$,

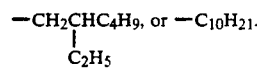

9. The composition according to claim 1, wherein said ester of a polyhaloaromatic acid may additionally contain other brominated and/or chlorinated flame retardants.

10. The composition according to claim 9, wherein said brominated flame retardants are selected from the group consisting of

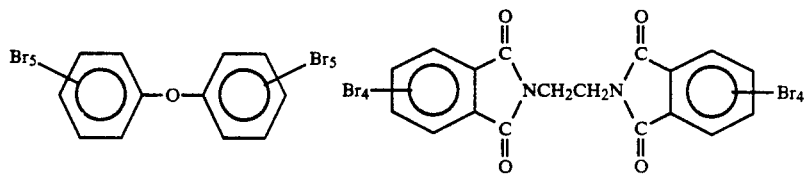

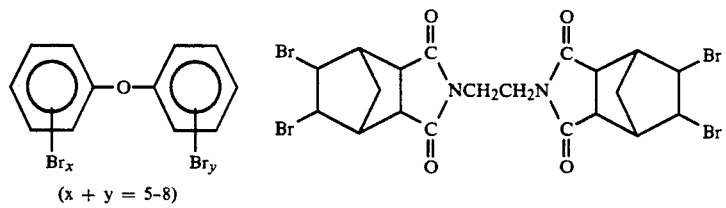

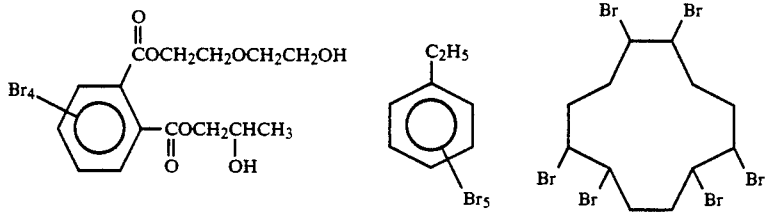

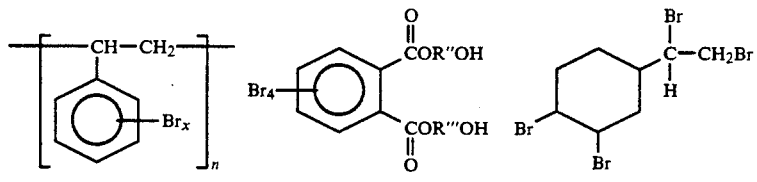

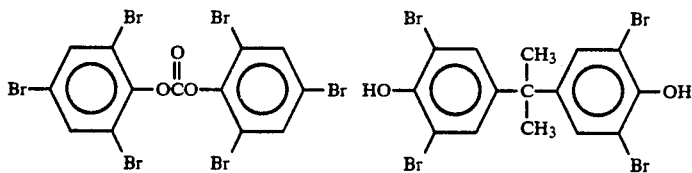

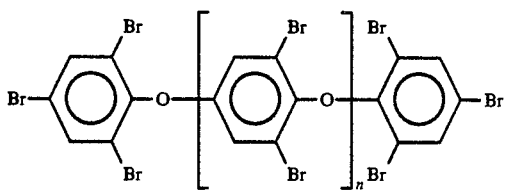

-continued

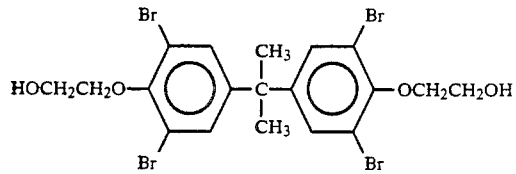

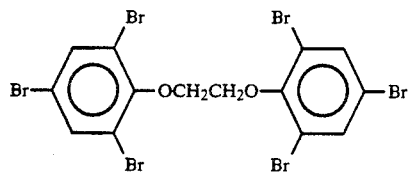

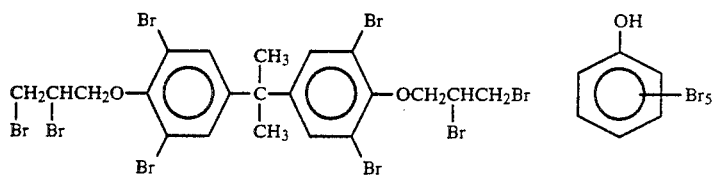

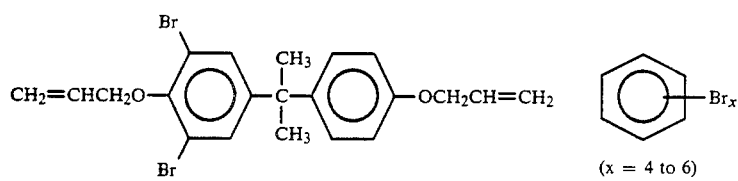

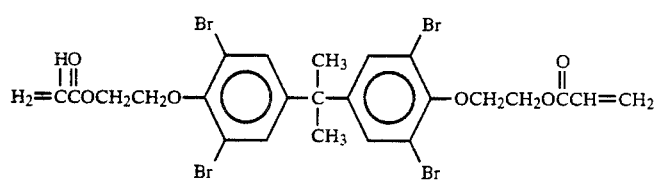

(x = 4 to 6)

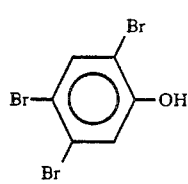

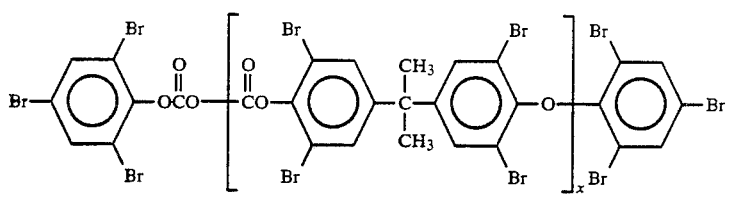

x ≈ 5.

11. The composition of claim 9 wherein R is an alkyl or substituted alkyl of 1 to 10 carbons, A is Br, m is 4, X is oxygen, p is 0 to 20, and q is 1 to 6.

12. The composition of claim 11, wherein R and $R^1$ are independently selected from: —$CH_3$, —$C_2H_5$, —$C_3H_7$, —$C_4H_9$, —$C_6H_{13}$, —$C_8H_{17}$, —$CH_2CHC_4H_9$, or —$C_{10}H_{21}$.
  |
  $C_2H_5$ 13. The composition according to claim 4, wherein said ester of a polyhaloaromatic acid may additionally contain other brominated and/or chlorinated flame retardants.

14. The composition of claim 13 wherein R is an alkyl or substituted alkyl of 1 to 10 carbons, A is Br, n is 4, X is oxygen, p is 0 to 20, and q is 1 to 6.

15. The composition of claim 14, wherein R and $R^1$ are independently selected from: —$CH_3$, —$C_2H_5$, —$C_3H_7$, —$C_4H_9$, —$C_6H_{13}$, —$C_8H_{17}$, —$CH_2CHC_4H_9$, or —$C_{10}H_{21}$.
  |
  $C_2H_5$

16. A composition according to claim 1, wherein said resin is polypropylene and said ester is di-2-ethylhexyl-tetrabromophthalate.

17. A composition according to claim 16, which also includes the flame retardant decabromodiphenyl oxide.

18. A composition according to claim 17 which also includes antimony oxide as a flame retardant synergist.

19. A composition according to claim 1, wherein said amount of ester is also sufficient to increase the processability of said resin.

20. A method for increasing the flame retardancy and processability of a polyolefin resin comprising uniformly blending with said resin a flame retarding amount of a polyhaloaromatic acid ester of the following general formula:

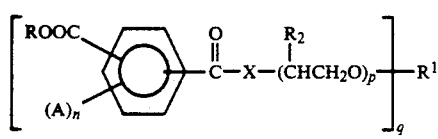

(I)

wherein
- (a) the ring can have all possible isomeric arrangements;
- (b) R is selected from the group consisting of alkyl or substituted alkyl of 1 to 30 carbons with the proviso that said alkyl is not substituted with a hydroxy group or a halogen, and

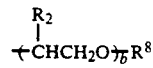

wherein $R^8$ is an alkyl or substituted alkyl of 1 to 18 carbons with the proviso that said alkyl is not substituted with a hydroxy group or a halogen, and b is 1 to 50;

- (c) $R^1$ is selected from the group consisting of alkyl or substituted alkyl of 1 to 30 carbons, alkenyl or substituted alkenyl of 2 to 22 carbons with the proviso that said alkyl and alkenyl are not substituted with a hydroxy group or a halogen,

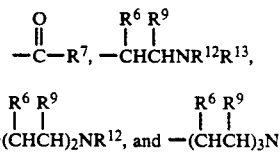

with the proviso that the valence of $R^1$ is equal to q;
- (d) $R^2$ is independently selected from the group consisting of H and $CH_3$;
- (e) $R^6$, $R^9$, $R^{12}$ and $R^{13}$ are independently hydrogen or alkyl of 1 to 22 carbons, $R^7$ is an alkyl of 1 to 18 carbons;
- (f) p is an integer of 0 to 50;
- (g) q is an integer of 1 to 6;
- (h) A is halogen;
- (i) X is O or NH; and
- (j) n=1 to 4.

* * * * *